(12) United States Patent
Branco de Luca et al.

(10) Patent No.: US 6,991,853 B2
(45) Date of Patent: Jan. 31, 2006

(54) BLANK FROM WHICH A CUSTOMIZED PROSTHETIC PART CAN BE MACHINED

(75) Inventors: Silvio Castello Branco de Luca, Rio de Janeiro (BR); Eduardo Cezar de Andrade de Mello e Souza, Rio de Janeiro (BR); Alexandre de Lima Spinola, Rio de Janeiro (BR); Eduardo da Rocha Albuquerque, Rio de Janeiro (BR); Mauricio Ladeira Casado, Niterói (BR)

(73) Assignee: Biogénie Projetos Ltda., Rio de Janeiro (BR)

( * ) Notice: Subject to any disclaimer, the term of this patent is extended or adjusted under 35 U.S.C. 154(b) by 0 days.

(21) Appl. No.: 10/446,933

(22) Filed: May 29, 2003

(65) Prior Publication Data

US 2004/0241464 A1    Dec. 2, 2004

(51) Int. Cl.
*A61C 8/00*    (2006.01)
(52) U.S. Cl. .................. 428/542.8; 433/49; 433/50; 433/201.1
(58) Field of Classification Search ............. 428/542.8, 428/131, 134, 135; 433/49, 50, 51, 201.1; 264/16, 19
See application file for complete search history.

(56) References Cited

U.S. PATENT DOCUMENTS

| | | | |
|---|---|---|---|
| 4,615,678 A | 10/1986 | Moermann et al. | |
| 5,652,709 A | 7/1997 | Andersson et al. | |
| 5,759,036 A * | 6/1998 | Hinds | 433/214 |
| 5,775,911 A * | 7/1998 | Hahn | 433/223 |
| 6,224,371 B1 | 5/2001 | De Luca | |
| 2005/0008989 A1 | 1/2005 | Rothenberger et al. | |

* cited by examiner

*Primary Examiner*—Jennifer McNeil
(74) *Attorney, Agent, or Firm*—Finnegan, Henderson, Farabow, Garrett & Dunner, L.L.P.

(57) ABSTRACT

A blank used for machining customized prosthetic components is provided which includes a prefabricated seating surface, normally shaped as an anti-rotation device, used to seat the component in the corresponding implanted, or natural, surface in the patient's body. Prosthetic components need to be custom manufactured because each patient presents a different need, however, the standardized shape of seating surfaces allows for these to be machined in large scale, without affecting the quality of the treatment the patient receives. Once the customized manufacturing has been completed around the seating surface, the part requires no further machining and is ready to be used.

30 Claims, 4 Drawing Sheets

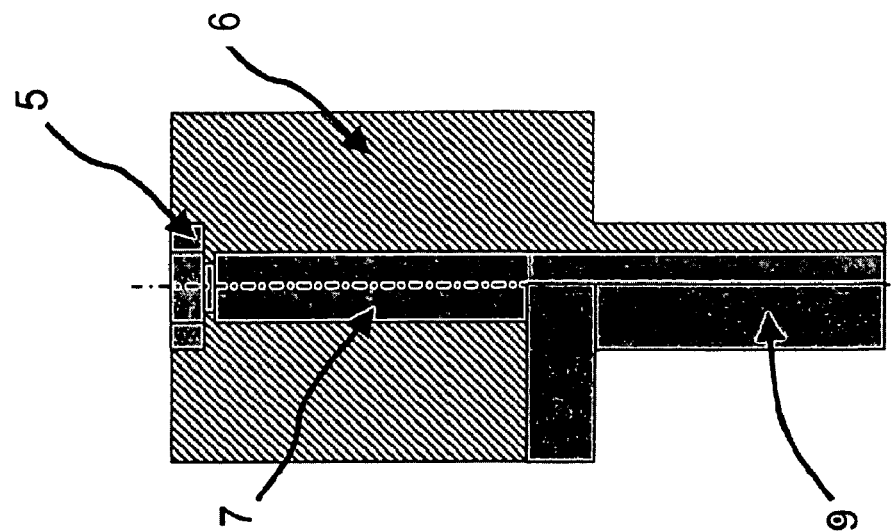
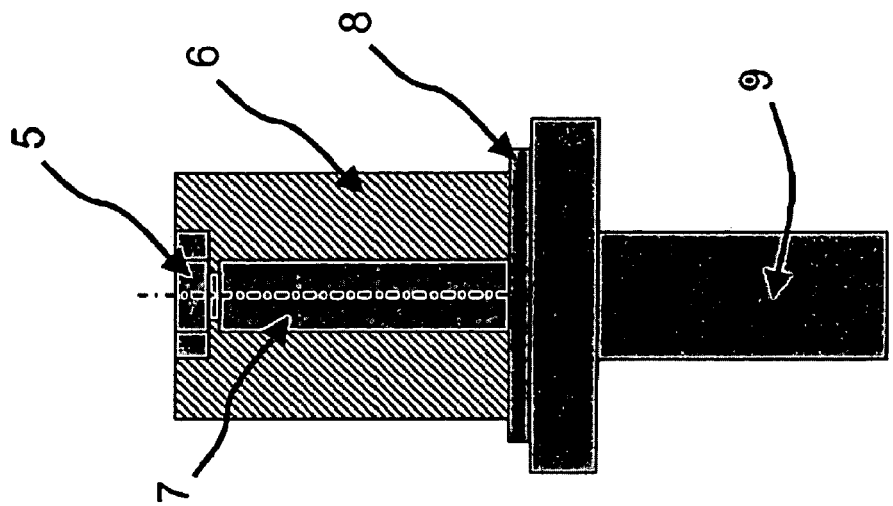
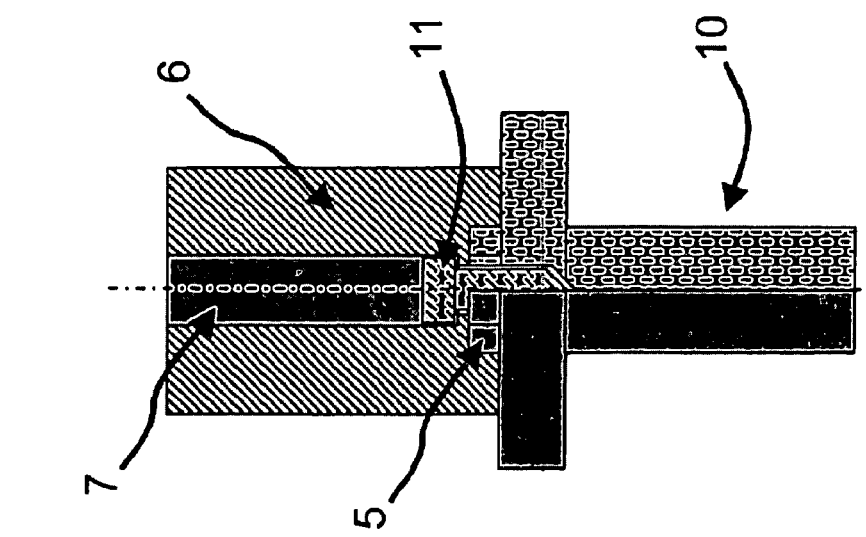

BLANK FROM WHICH A CUSTOMIZED PROSTHETIC PART CAN BE MACHINED

FIELD OF THE INVENTION

The present invention relates to a blank used to manufacture customized prosthetic components, more particularly, abutments of dental prosthetic replacements.

BACKGROUND OF THE INVENTION

The present invention relates to a blank that facilitates the rapid and economical production of dental prosthetic components. Dental prosthetic components, nonmally made from ceramic or metallic materials, are used to functionally substitute a part of a patient's dentition. There are three major components used in a complete prosthetic restoration, a substitute for the tooth's root (called a fixture), a substitute for a tooth's internal structure (called an abutment), and a cosmetic substitute, which replaces the tooth's appearance. Some patient's may need only cosmetic substitutes while others need a full replacement.

Normally, when a patient needs a prosthetic replacement, several surgical and laboratory steps must be completed before the actual replacement is ready to be installed. These steps range from installing anchors into the patient's bones to fabricating the prosthetic replacement itself. One thing that must be understood is that regardless of the kind of treatment the patient is undergoing, time is the crucial element. The longer it takes to properly treat a medical condition, the further the scenario deteriorates, thus the bigger the problem that needs resolving. Recent developments ill the art have allowed for cosmetic substitutes (namely crowns, bridges, or inlays) to be manufactured by CAD/CAM devices, directly in the dentist's office (sometimes referred to as chair-side systems), thus shortening the time between a patient's admittance to his release. However helpful, cosmetic replacements are seldom used alone, and treatments that require other prosthetic components must still endure the delays involved in fabricating the remaining components. The main reason current chair-side CAD/CAM systems cannot manufacture abutments or fixtures is the high degree of precision required to manufacture the connecting elements, which join prosthetic components together ensuring their proper alignment and securing them form rotating once installed. Since most chair-side systems cannot achieve said high degree of precision during milling, these machines cannot produce abutments or fixtures using their current blanks. The present invention pre-integrates the connecting element into the design of the blank that will be milled, thus helping to further reduce the time needed to treat a patient, once it allows for the remaining dental prosthetic components to be manufactured inside the dental office, often using the same CAD/CAM equipment already applied in making the cosmetic parts.

SUMMARY OF THE INVENTION

The present invention allows for the fast and economical production of customized dental prosthetic components, by providing a blank with pre-fabricated connecting elements. Since connecting elements have standardized dimensions with few discrete variations, they can be easily mass-produced into the blanks. By pre-fabricating the connecting element into the blank's design, all that remains to be done in the dental office is to custom form the outer part of the blank according to the specific need of the patient. This operation is much simpler, and can be achieved with most of the currently available CAD/CAM systems for the dental office. In this sense, a blank used for machining customized prosthetic components is provided which includes a prefabricated seating surface, normally shaped as an anti-rotation device, used to seat the component in the corresponding implanted, or natural, surface in the patient's body The connecting element of a prosthetic component is the geometry used to align and lock the element from rotating relative to a joined second prosthetic component, these are often presented as hexagonal connectors or Morse Cones, but other geometries may also be applied. For example, fixtures (which are installed into the patient's bone) may have an hexagonal connecting element and a corresponding abutment (the part that replicates the tooth's internal structure) would have the corresponding hexagonal connecting element, when coupled together, the joined connecting elements from both parts would prevent the parts from rotating thus maintaining alignment between the parts. Depending on the dental reconstruction, parts with more than one connecting element may be required. The present invention also resolves this situation because the blank can have more than one connecting element. In the case of multiple connecting elements, a template would have to be used during the surgical procedure (installation of the fixture) to ensure proper alignment later on.

In order to facilitate the milling operation of a prosthetic component, the blank must also include a support geometry, used to fasten the blank in the milling machine that will perform the customization. This support geometry may range from a simple elongation of the stub, to more complex one-step-locking designs. An example of one-step-locking design would be a Morse-Cone, where the geometry forces the part to lock once it's put into place.

Finally, the blank must include the access paths for fastening screws, which will be used later to secure the different prosthetic components together.

BRIEF DESCRIPTION OF THE DRAWINGS

Briefly, FIG. 4 shows the supporting element from related U.S. Pat. No. 6,224,371, joined with the blank proposed in this invention; finally FIGS. 5–10 show variations of the present invention.

FIG. 1: resents the supporting stub currently used to fasten blanks in milling machines;

FIG. 2: Shows the block from which the actual final crown, bridge, or inlay will be cut is shown cemented to the supporting stub shown in FIG. 1;

FIG. 3: Presents a variation of the current state of the art where the supporting stub already is made from the material from which the final part will be cut;

FIG. 4: Shows the support stub containing the connecting element presented in related U.S. Pat. No. 6,224,371, along with the blank containing the connecting element presented in this invention;

FIG. 5: Illustrates a variation of the present invention where the blank containing the connecting element is cemented to the supporting stub;

FIG. 6: Presents a variation of the present invention where the blank containing the connecting element includes the support geometry;

FIGS. 7 and 8: Show variations of FIGS. 5 and 6, where the connecting elements are pre-fabricated in a different face of the blank;

FIG. 9: Schematically represents a prosthetic component cut from the blank proposed in the present invention;

FIG. 10: Illustrates the blank from the present invention with more than one connecting element, and a schematic representation of a prosthetic component to be cut from the blank.

DETAILED DESCRIPTION OF THE INVENTION

Figures 1, 2, 3:
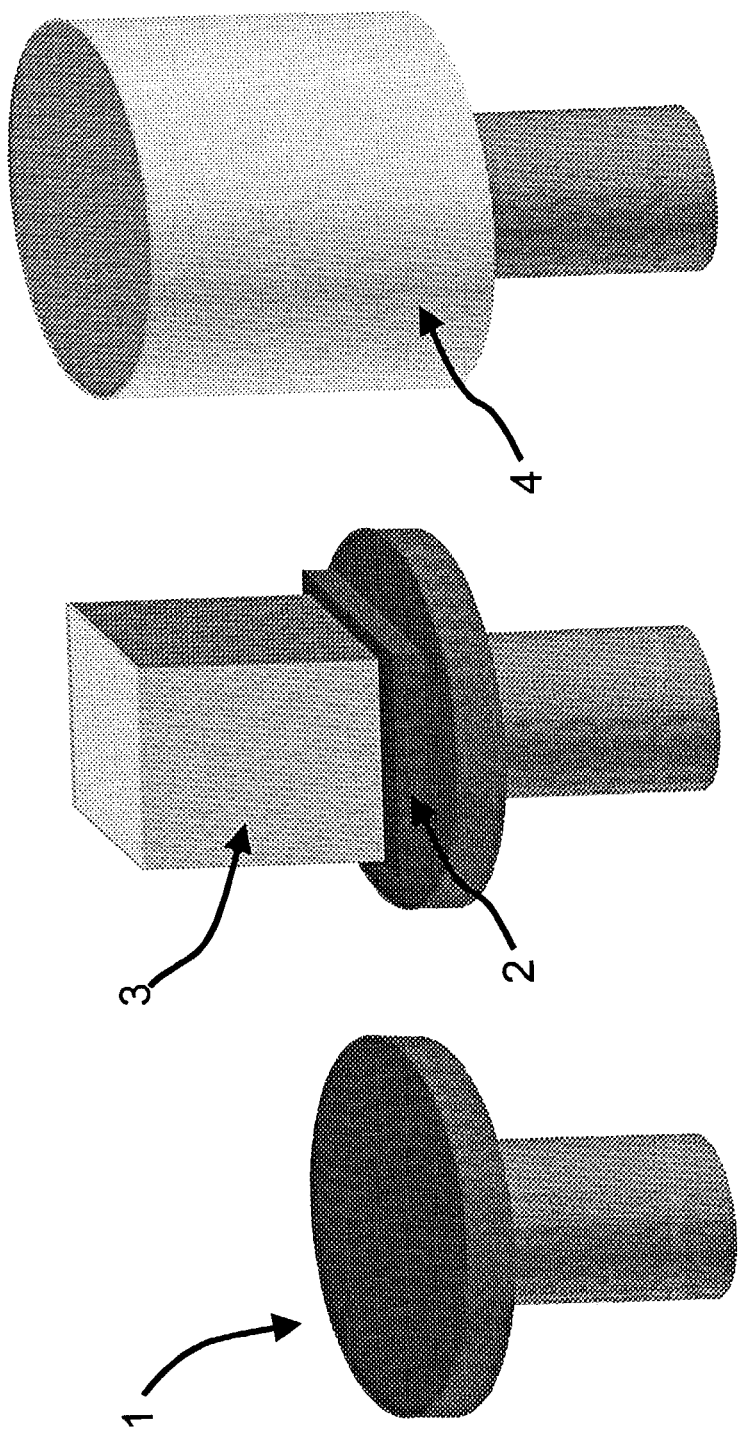
FIGS. 1, 2, and 3 show current state of the art on blanks for milling dental crowns, bridges or inlays.

Improvements in the art include allowing for final parts to be cut at a low cost, directly where the part will be used. The pre-fabrication of connecting elements (5) into the blanks (FIGS. 4 to 10) exclude the need for any future milling on the part, once customization is done, thus simplifying the build process for a prosthetic component.

When designing the blank, the critical characteristic is the connecting element (5), other shape defaults, such as outer shape, aren't as critical and can be provided in such a way that best suit's the user's requirements. The general orientation between blank and connecting elements, that is the direction (or surface) where it occurs on the blank is not a factor in fixating the blank to the milling machine. The blank proposed in this invention can be fastened to the milling machine by any of its surfaces, and, similarly, the connecting element can appear pre-fabricated in any of the blank's surfaces.

FIG. 4 shows the support stub (10) containing the connecting element presented in related U.S. Pat. No. 6,224,371, along with the blank (6) containing the connecting element (5) and access path (7) for fastening screw (11) presented in this invention.

FIG. 5 Presents a variation of the present invention where the blank (6) containing the connecting element (5) and access path for screws (7) is cemented (8) to a supporting stub (9) similar to (1).

FIG. 6 Presents a variation of the present invention where the blank (6) containing the connecting element (5) and access path for screws (7) includes the support geometry (9).

Figure 8:
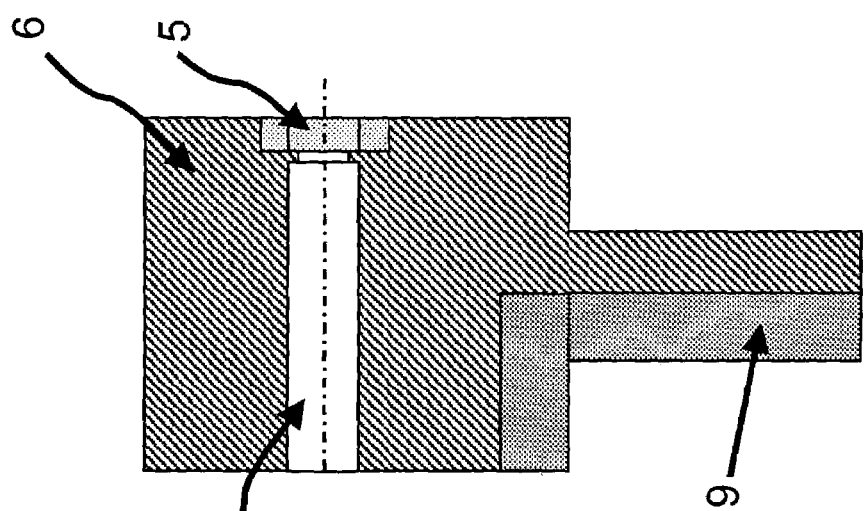
Figure 7:
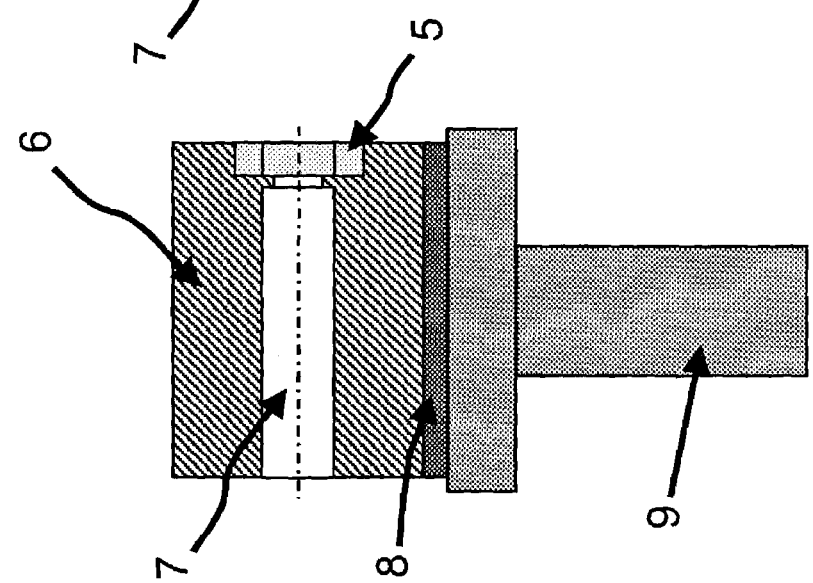

FIGS. 7 and 8, Present variations of FIGS. 5 and 6, where the connecting elements (5) are pre-fabricated in a different face of the blank.

Moërmann et al. described in U.S. Pat. No. 4,615,678 a blank, shown in FIG. 2, that allowed the milling of prosthetic components on location, that blank, however included two parts that where cemented (2) together, a block (3) from which the final piece would be cut, and a supporting stub (1), shown in FIG. 1. A variant type blank (4) (shown in FIG. 3) composed exclusively of one kind of material, is used in some CAD/CAM systems (an example of which would be Cynovad) to fabricate crowns and bridges, but doesn't allow abutments to be milled because it lacks the presence of a connecting element. Other examples available in industry, generally present the same ability to perform inlays, crowns and bridges, but lack the expansion potential to abutments because they lack the connecting element.

The improvement in the art presented by this invention, allows for CAD/CAM machines, currently limited in their ability to manufacture prosthetic components, to expand their universe of possibilities into the realm of abutments and fixtures.

Figure 9:
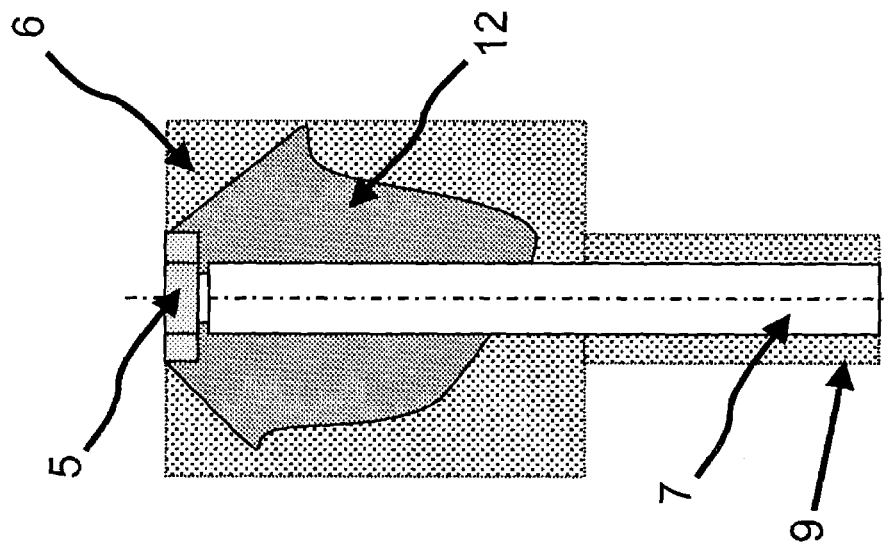

FIG. 9 Schematically represents a prosthetic component (12) cut from the blank (6) proposed in the present invention. The blank is attached to the milling machine through the support geometry (9) so that its securely fastened and can be properly cut. Notice the presence of the pre-fabricated connecting element (5) at the base of the finalized part, along with access path (7) for the screw that will later be used to fasten this component to other prosthetic parts.

Figure 10:
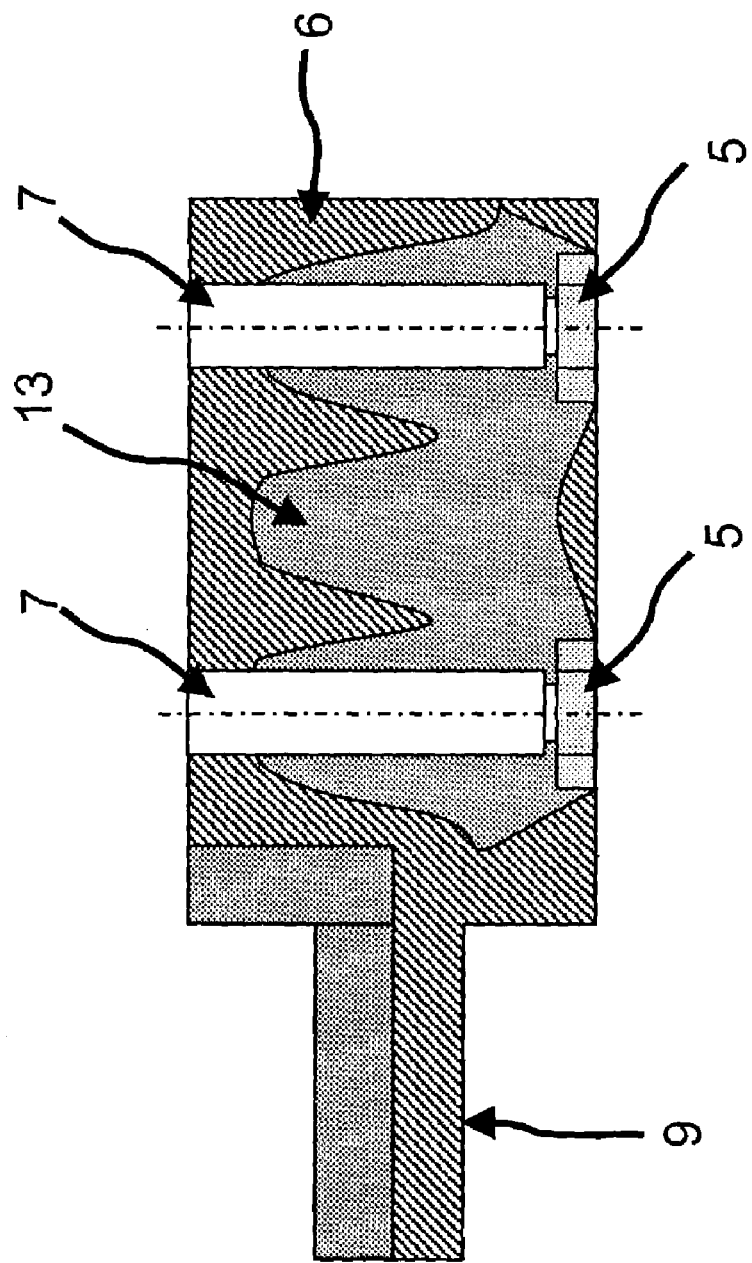

FIG. 10, presents the blank (6) from the present invention with more than one connecting element (5), and a schematic representation of a prosthetic component (13) to be cut from the blank (6). Once again, notice the presence on the pre-fabricated connecting elements (5) and screw paths (7) in the final part (13). This variant of the proposed blank also contains a support geometry (9) so that it can be properly attached to the milling machine.

Whereas co-owned U.S. Pat. No. 6,224,371 proposes a supporting device, the present invention relates to the entire blank, part which will actually be cut. This blank (6) may be composed of different kinds of biocompatible materials, normally Titanium or ceramic type materials are used, Biomaterials (including human or bovine Demineralized Freeze Bone Dry Allograft (DFBDA); human or bovine Freeze Bone Dry Allograft (FBDA); or, synthetic or coral hydroxyapatite, amongst others currently being developed) may also be applied, but ultimately the material that should be used is the one that best suits the patients' need.

What is claimed is:

1. A blank from which a prosthetic component can be formed, comprising:
    a blank body made from a biocompatible material;
    the blank body having a component portion including at least three surfaces and a support portion connected to one of the at least three surfaces of the component portion;
    an unconnected surface of the component portion forming a pre-fabricated seating surface, the pre-fabricated seating surface including at least one anti-rotation element; and
    at least one access path for receiving a fastening screw.

2. The blank of claim 1 wherein the biocompatible material is Titanium.

3. The blank of claim 1 wherein the biocompatible material is a ceramic material.

4. The blank of claim 1 wherein the biocompatible material is a biomaterial.

5. The blank of to claim 1 wherein the at least one anti-rotation element is hexagonal in shape.

6. The blank of claim 1 wherein the at least one anti-rotation element is shaped as a Morse-Cone.

7. The blank of claim 1, wherein the support portion is attached to the component portion by a chemical compound.

8. The blank of claim 7, wherein the component portion includes a top surface, a bottom surface, and a multi-sided surface.

9. The blank of claim 8, wherein the at least one pre-fabricated seating surface is the top surface.

10. The blank of claim 8, wherein the at least one pre-fabricated seating surface is the bottom surface.

11. The blank of claim 8, wherein the at least one pre-fabricated seating surface is a side of the multi-sided surface.

12. The blank of claim 1, wherein the chemical compound is a cement.

13. The blank of claim 1, wherein the component portion includes a top surface, a bottom surface, and a cylindrical surface.

14. The blank of claim 13, wherein the at least one pre-fabricated seating surface is the top surface.

15. The blank of claim 13, wherein the at least one pre-fabricated seating surface is the bottom surface.

16. The blank of claim 13, wherein the at least one pre-fabricated seating surface is the cylindrical surface.

17. A blank from which a prosthetic component can be formed, comprising:
- a blank body having a first support portion and a second component portion, wherein the first and second portions are integrally formed from a single piece of material and positioned adjacent one another, the blank body being made from a biocompatible material;
- a portion of an outer surface of the blank body forming a pre-fabricated seating surface, the pre-fabricated seating surface including at least one anti-rotation element; and
- at least one access path configured to receive a fastening screw for securing the prosthetic component.

18. The blank of claim 17, wherein the blank body includes a top outer surface, a bottom outer surface, and a cylindrical outer surface.

19. The blank of claim 18, wherein the at least one pre-fabricated seating surface is the top outer surface.

20. The blank of claim 18, wherein the at least one pre-fabricated seating surface is the bottom outer surface.

21. The blank of claim 18, wherein the at least one pre-fabricated seating surface is the cylindrical outer surface.

22. The blank of claim 17, wherein the blank body includes a top outer surface, a bottom outer surface, and a multi-sided outer surface.

23. The blank of claim 22, wherein the at least one pre-fabricated seating surface is the top outer surface.

24. The blank of claim 22, wherein the at least one pre-fabricated seating surface is the bottom outer surface.

25. The blank of claim 22, wherein the at least one pre-fabricated seating surface is one of the sides of the multi-sided outer surface.

26. The blank of claim 17, wherein the biocompatible material is Titanium.

27. The blank of claim 17, wherein the biocompatible material is a ceramic material.

28. The blank of claim 17, wherein the biocompatible material is a biomaterial.

29. The blank of claim 17, wherein the at least one anti-rotation element is hexagonal in shape.

30. The blank of claim 17, wherein the at least anti-rotation element is a shaped as a Morse-Cone.

* * * * *

UNITED STATES PATENT AND TRADEMARK OFFICE
CERTIFICATE OF CORRECTION

PATENT NO.    : 6,991,853 B2
DATED         : January 31, 2006
INVENTOR(S)   : Branco de Luca et al.

It is certified that error appears in the above-identified patent and that said Letters Patent is hereby corrected as shown below:

Column 4,
Line 41, "blank of to claim" should read -- blank of claim --.

Column 6,
Lines 20-21, "the at least anti-rotation element" should read -- the at least one anti-rotation element --.
Line 21, "element is a shaped as" should read -- element is shaped as --.

Signed and Sealed this

Twenty-fifth Day of April, 2006

JON W. DUDAS
*Director of the United States Patent and Trademark Office*